United States Patent

Tardy et al.

[11] Patent Number: 6,165,488
[45] Date of Patent: Dec. 26, 2000

[54] ADHESIVE COMPOSITION WITH MACROMOLECULAR POLYALDEHYDE BASE AND METHOD FOR CROSS-LINKING COLLAGEN

[75] Inventors: Michel Tardy; Hervé Volckmann; Jérôme Tiollier, all of Lyons; Philippe Gravagna, Irigny; Jean-Louis Tayot, La Tour de Salvagny, all of France

[73] Assignee: Societe Anonyme de Developpement des Utilisations du Collagene S.A.D.U.C., Chaponost, France

[21] Appl. No.: 09/091,050

[22] PCT Filed: Oct. 7, 1997

[86] PCT No.: PCT/FR97/01787

§ 371 Date: Jun. 8, 1998

§ 102(e) Date: Jun. 8, 1998

[87] PCT Pub. No.: WO98/15299

PCT Pub. Date: Apr. 16, 1998

[30] Foreign Application Priority Data

Oct. 7, 1996 [FR] France ................... 96 12200
Dec. 23, 1996 [FR] France ................... 96 15888

[51] Int. Cl.$^7$ ........................................ A61F 2/02
[52] U.S. Cl. ............................................. 424/426
[58] Field of Search .................................. 424/426

[56] References Cited

U.S. PATENT DOCUMENTS 3,057,723 10/1962 Jeffreys et al. .
4,970,298 11/1990 Silver et al. ................... 530/356

OTHER PUBLICATIONS

"Gelatin–based adhesives for bookbinding", *Chemical Abstracts*, Abstract No. 85407, vol. 116, No. 10, Mar. 9, 1992.

"Some Aspects of the Crosslinking of Gelatin by Dextran Dialdehydes", Schacht, et al. *Polymer Gels and Networks*, vol. 1, 1993, pp. 213–224.

*Primary Examiner*—Carlos A. Azpuru
*Attorney, Agent, or Firm*—Larson & Taylor plc

[57] ABSTRACT

A biocompatible, bioresorbable and nontoxic adhesive composition for surgical and/or therapeutic use, especially for the bonding of biological tissues to one another or to an implanted biomaterial, is provided which comprises at least one biodegradable macromolecular polyaldehyde of natural origin in aqueous solution and a collagen-based component dissolved in aqueous medium. A process for preparing this composition is also provided wherein these aqueous components are mixed together (e.g., at neutral, physiological pH) to give a gel which is rapidly applied to tissues and/or biomaterial to achieve binding. The present invention is advantageous in that it provides biodegradable macromolecular polyaldehydes with adhesive properties and the ability to be extremely well tolerated by the recipient while retaining their adhesive properties during their retention in the body. The invention thus makes it possible to rapidly bind biological tissues to one another or to implanted biological material without tissue lesions in a manner which also retains the quality and the mechanical strength of the adhesion.

66 Claims, No Drawings

ADHESIVE COMPOSITION WITH MACROMOLECULAR POLYALDEHYDE BASE AND METHOD FOR CROSS-LINKING COLLAGEN

This is a Rule 371 continuation of PCT application PCT/FR97/01787, filed Oct. 10/7/97.

BACKGROUND OF THE INVENTION (1) Field of the Invention

The present invention lies in the field of biodegradable and nontoxic biological adhesives intended for surgical or therapeutic use.

More precisely, the present invention deals with a biocompatible, bioresorbable and nontoxic adhesive composition based on at least one macromolecular polyaldehyde.

It also relates to such an adhesive composition additionally comprising a collagen-based component.

It also relates to a process for crosslinking solubilized collagen which makes it possible to obtain an adhesive material intended to be applied quickly to tissues and/or a biomaterial.

(2) Description of the Related Art

The crosslinking of collagen can be carried out either by a chemical route, with the aid of tanning agents such as glutaraldehyde or formaldehyde or alternatively diisocyanate or other reactants, or by using physical agents such as gamma, beta or ultraviolet radiations.

However, this last method is cumbersome and sometimes difficult to implement and, besides the crosslinking, it also produces scissions.

Insofar as the chemical route is concerned, treatment with glutaraldehyde (or formaldehyde) is the treatment most frequently employed for crosslinking collagen and consists in immersing powders, films, gels or more or less concentrated solutions of collagen in a solution of glutaraldehyde. It has a certain number of disadvantages, depending on the applications. The introduction of glutaraldehyde into an aqueous collagen-based structure can especially entail a rapid separation of excess glutaraldehyde by diffusion through the gel formed.

In surgery or therapy this gives rise to toxic reactions, resulting in tissue necrosis or less severe reactions, leading to poor or retarded cicatrization. This is the case with the collagen-based adhesive available on the market today.

In this adhesive, called GRF, the crosslinking of gelatin is produced by formaldehyde in the presence of resorcinol, the latter being used essentially to reduce the dissolving of the adhesive mass. This adhesive has been employed between the 1960s and the 1980s, but, in fact, its use in surgery is now restricted to a few rare applications where the benefit exceeds the risks (aortic dissection) because of the possibility of separation of the formaldehyde and because of its toxicity. An excessive quantity of formaldehyde is needed to obtain rapid crosslinking of the collagen-based gel and good adhesion to the surrounding tissues. This excess of formaldehyde is responsible for the poor biocompatibility of the GRF adhesive. It is therefore not possible today to generalize the use of this adhesive to the cicatrization of surgical or chronic wounds, to the protection or the leakproofing of sutures or to the release of medications.

A recent improvement has just been proposed, by increasing the viscosity of the medium which contains the formaldehyde, the glutaraldehyde or other dialdehyde by adding a gelling agent such as agar (G. Izoret patent application, Wo 96/14368). However, this does not eliminate the risk of diffusion of the crosslinking agent, even though the diffusion is slowed down.

Furthermore, the biocompatibility of collagen crosslinked with toxic chemical agents can be improved by reducing the quantity of crosslinking agents employed to a minimum. This is what is done in preformed materials intended to be implanted, where the reaction time can be prolonged as much as necessary by the manufacturer of the material. In this case small quantities of crosslinking agent are employed and the crosslinked material is carefully washed at the end of preparation to remove any excess of reactant.

The final crosslinked material employed by the surgeon is in this case a solid or a suspension of collagen-based fibres, but these materials are devoid of adhesiveness to the surrounding tissues.

The preparation of a biological adhesive often requires the mixing, by the surgeon himself, in contact with the biological tissues to be treated, of two different solutions permitting a rapid crosslinking of the collagen, of the gelatin or of any other reactive macromolecule or molecule.

For example, the adhesive marketed by the Immuno company under the name of "Tissucol" (Tisseel) and then by Behringwerke under the name of "Beriplast" and by Biotransfusion under the name of "Biocol" is known. This is a concentrated solution of fibrinogen (70–140 mg/ml) containing Factor XIII and fibronectin, the polymerization of which is induced by a solution of thrombin (4 to 400 International Units) in an extemporaneous mixture. The fibrinogen subsequently polymerizes to fibrin to reform a coagulum which ensures the adhesion of the tissues brought into contact.

The difficulties and major problems raised by this product and its components are, on the one hand, the absence of complete characterization and reproducibility of the quantity of each of the components of the fibrinogen solution (Factor XIII, fibronectin, aprotinin) and, on the other hand, the difficulty in viral inactivation of such a product with regard to uncoated viruses like Unconventional Transmissible Agents. This has led to a restriction on the possibility of employing such products on a large scale.

Tardy et al. (French patent application No. 9400715) have described a collagen-based biological adhesive which can be prepared by virtue of a kit consisting, for example, of two separate syringes containing, respectively, a solution of collagen (or gelatin) oxidized with sodium periodate and stored at acidic pH in frozen form at a temperature lower than 0° C., preferably of the order of −20° C., and an aqueous alkaline solution. The mixing of the respective contents is ensured by a mixer connected to the two syringes, after the oxidized collagen (or gelatin) gel has been reheated to about 40° C., in order to obtain a biocompatible adhesive whose crosslinking is accomplished in 2 to 3 minutes.

The properties of this adhesive are advantageous in some applications, but the main problem with this technology is the need for a complex cold system for the distribution of this product, which increases its cost and makes it awkward to use in premises not equipped with a deep-freeze.

It has also been proposed to employ reactive polyethylene glycol derivatives to form biological adhesives based on albumin or collagen (Barrows et al. patent No. WO 96 031 59 Al; D. Sierra—Tissue Sealants Meeting La Jolla, 1996). However these reactants are not very stable in water and can require special storage methods. Their optimum activity pH is alkaline, not physiological. Furthermore, the resorption period of these products is very long, longer than 3 to 4 weeks and this, in some applications, is a major disadvantage.

The incontrovertible need to obtain, rapidly and sometimes virtually instantaneously, the solidification of a fluid solution in order to obtain a strong adhesion, can make it necessary to employ an excess of chemical crosslinking reactants, which results in toxicity and in mediocre tissue biocompatibility.

Tissue adhesives based on commercial gelatin and on oxidized starch or glutaraldehyde have also been recently proposed in the document Wo 97/29715 (Fusion Medical Technologies Inc.).

These adhesives form very viscous gels which have to be heated to a high temperature, of the order of 50–80° C., in order to be applied with a syringe.

Besides the risk of potential toxicity depending on the aldehyde used, these adhesives can damage the treated tissues, in particular because of their application temperature.

BRIEF SUMMARY OF THE INVENTION

The objective of the invention is to provide an adhesive composition which does not exhibit the major disadvantages referred to above.

Its objective is thus to provide a biocompatible, bioresorbable and nontoxic adhesive composition suitable for a surgical and/or therapeutic use, which is stable in time and which can be stored in relatively simple conditions while being easy to employ, especially injectable with the aid of needles or catheters.

It is also its objective to provide an adhesive composition exhibiting improved adhesion and mechanical strength properties.

Another objective of the invention is, in particular, to provide an adhesive composition with which the crosslinking of collagen or of gelatin takes place very rapidly and whose rate can be easily modified.

Another objective is also to provide an adhesive composition which does not exhibit any toxicity risks, in particular due to diffusion of the crosslinking agent.

An objective of the invention is also to provide an adhesive composition for bonding biological tissues, including living tissues, to one another or with an implanted biomaterial which can be the adhesive itself (used on its own).

The invention has furthermore an objective of providing a process for crosslinking collagen (or gelatin) making it possible to obtain especially such an adhesive composition, which is easy to implement and poses no threat to the recipient body.

Another objective of the invention is to provide kits including an adhesive composition as mentioned above, for surgical and/or therapeutic use, which is simple and practical to utilize.

DETAILED DESCRIPTION OF THE INVENTION

To this end, the subject-matter of the invention is a biocompatible, bioresorbable and nontoxic adhesive composition for surgical and/or therapeutic use, especially for the bonding of biological tissues to one another or to an implanted biomaterial, characterized in that it includes at least one biodegradable macromolecular polyaldehyde of natural origin, such as oxidized starch or a polyaldehyde having similar stability properties.

It is believed that the stability of such aqueous solutions is obtained, naturally, by the fact that the solution becomes spontaneously acidic.

The subject-matter of the invention is thus in particular such compositions including a polyaldehyde in aqueous solution at the acidic pH naturally obtained or in the acidic freeze-dried form.

Another subject-matter of the invention is an adhesive composition, characterized in that it includes: on the one hand, a collagen-based component dissolved in aqueous medium, selected from unhydrolysed collagen having at least partially lost its helical structure, mainly composed of $\alpha$ chains, native collagen according to a concentration of less than 5%, and on the other hand, at least one biodegradable macromolecular polyaldehyde of natural origin in aqueous solution as defined above.

The invention also provides a process for the preparation of a biocompatible, bioresorbable and nontoxic adhesive for surgical and/or therapeutic use intended to be applied to tissues and/or a biomaterial, characterized in that it includes the stage consisting in mixing, with a collagen-based component dissolved in aqueous medium selected from unhydrolysed collagen having at least partially lost its helical structure, composed essentially of $\alpha$ chains, native collagen according to a concentration of less than 5%, prior to its crosslinking, at least one biodegradable macromolecular polyaldehyde of natural origin in aqueous solution at the pH as defined above.

The invention also has as its subject-matter the use of biodegradable macromolecular polyaldehyde of natural origin in aqueous solution as defined above for obtaining a biocompatible, bioresorbable and nontoxic adhesive composition for surgical and/or therapeutic use, especially for the bonding of biological tissues to one another or to an implanted biomaterial exhibiting amine-containing reactive functional groups opposite the said polyaldehyde.

The invention also has as its subject-matter the use of such a polyaldehyde in combination with a collagen-based component as defined above, in aqueous solution.

Finally, the invention has as a subject-matter kits for biocompatible, bioresorbable and nontoxic adhesive composition, which are intended for a surgical and/or therapeutic use, characterized in that they include:

an aqueous solution containing at least one biodegradable macromolecular polyaldehyde of natural origin, as defined above.

The invention has also as a subject-matter kits for adhesive composition including:

an aqueous solution of a collagen-based component selected from unhydrolysed collagen having at least partially lost its helical structure, mainly composed of $\alpha$ chains, native collagen according to a concentration of less than 5%;

an aqueous solution containing at least one biodegradable macromolecular polyaldehyde of natural origin, as defined above, means of mixing for extemporaneously mixing the said solutions.

The invention has also as a subject-matter a process for bonding a biomaterial to biological tissues, characterized in that an aqueous solution containing at least one biodegradable macromolecular polyaldehyde of natural origin, as defined above, is applied to the said tissues and/or to the said biomaterial at a temperature of between 20 and 45° C., the said biomaterial exhibiting functional groups, especially amine-containing functional groups, which are reactive towards the said polyaldehyde.

The invention has also as a subject-matter a process for bonding biological tissues to one another or to an implanted biomaterial, characterized in that:

an aqueous solution of a collagen-based component selected from:

unhydrolysed collagen having at least partially lost its helical structure, mainly composed of α chains;

native collagen according to a concentration of less than 5%;

and an aqueous solution containing at least one biodegradable macromolecular polyaldehyde of natural origin, as defined above, are mixed at neutral, physiological pH;

the gel obtained is rapidly applied to the said tissues and/or the said biomaterial, the biomaterial exhibiting functional groups, in particular amine-containing functional groups, which are reactive towards the said macromolecular polyaldehydes, at a temperature of between 20 and 45° C.; and the said mixture is left to polymerize.

The inventors have discovered, quite unexpectedly, the potentially adhesive properties of such biodegradable macromolecular polyaldehydes of natural origin on living tissues and the ability of the adhesives stemming therefrom to be extremely well tolerated by the recipient body while retaining their adhesive properties during their retention in the body.

They have thus discovered that it is possible to bond biological tissues, including living tissues, to one another or with an implanted biomaterial, the latter having functional groups which are reactive towards macromolecular polyaldehydes, especially amine-containing functional groups.

The inventors have surprisingly discovered that it is possible to obtain a biological adhesive by bringing the excess of chemical reactants needed for the crosslinking of certain collagens or gelatins in the form of such a biodegradable macromolecular polyaldehyde and that this adhesive is effectively applicable to living tissues at a temperature close to physiological temperature, resulting in no tissue lesion, and has improved properties, especially in respect of the quality of adhesion and of mechanical strength.

According to the invention, "biodegradable macromolecular polyaldehyde of natural origin" is understood to mean any compound exhibiting several aldehyde functional groups which is derived from a natural biodegradable polymer.

The term "biodegradable" denotes a macromolecular polyaldehyde capable of disappearing by gradual degradation (metabolization).

The macromolecular polyaldehyde can be easily prepared by oxidation of polysaccharides or of mucopolysaccharides especially with periodic acid or its salts, according to a process which has been known per se for a very long time. Such preparations of oxidized polysaccharide have already been proposed in the past for crosslinking and stabilizing solid collagen-based materials in old documents (Johnson & Johnson patent U.S. Pat. No. 3,093,439 and Unilever U.S. Pat. No. 1,109,509), or gelatin dissolved in buffer medium.

However, the inventors have discovered that on employing such a crosslinking agent the phenomenon of diffusion of the latter was not observed, a phenomenon which is highly problematic in known biological adhesives, especially the GRF adhesive, in particular from the viewpoint of toxicity and of tissue biocompatibility.

They have discovered in particular that the macromolecular polyaldehyde, while introducing the necessary quantity of aldehyde into the collagen or gelatin solution, will be trapped within the adhesive gel which it will have allowed to form.

The macromolecular polyaldehyde used according to the invention consists advantageously of an oxidized polysaccharide or mucopolysaccharide.

The polysaccharide advantageously has a molecular weight of between 10 000 and 2 million daltons.

Among the polysaccharides or mucopolysaccharides which are suitable for carrying out the invention there may be mentioned starch, dextran, agar, cellulose, chitin, chitosan, alginic acid, glycosaminoglycans, hyaluronic acid and chondroitin sulphate or their derivatives.

According to the invention, starch and dextran are preferred, starch being most particularly preferred.

The polyaldehydes may be employed on their own or as mixtures.

The term "polyaldehyde" used according to the invention denotes without distinction a single polyaldehyde or a mixture of several polyaldehydes.

In accordance with the invention the polyaldehyde may result from the oxidation of an abovementioned compound with periodic acid or one of its salts, preferably sodium periodate, according to processes which are known per se.

For this to take place, a solution of periodic acid or of one of its salts is added to the polysaccharide or mucopolysaccharide solution until a concentration of between 0.01 and 1M, preferably 0.25 to 0.5M, is obtained.

The oxidation stage can be performed on solutions, gels or suspensions of polysaccharide(s).

The preparation of oxidized polysaccharide can next be subjected to dialyses, diafiltrations, filtrations or ultrafiltrations with the aim of removing the products of the oxidation reaction and reactants, as well as the iodine derivatives formed during the reaction or in excess.

It is also possible to envisage freeze-drying, it being possible for the redissolution of the lyophilisate to be carried out in water or with the necessary physiological buffer.

The adhesive composition according to the invention includes at least one biodegradable macromolecular polyaldehyde of natural origin as defined above.

It may be an aqueous solution including preferably from 0.5 to 5% by weight of polyaldehyde(s).

It has been found that the aqueous polyaldehyde solution becomes spontaneously acidic, which is favourable to its stability. In the presence of buffers which modify this pH, a gradual loss in reactivity over time is observed. The polyaldehyde is thus advantageously stored at the acidic pH which it naturally acquires in aqueous solution, until the time of use, or alternatively in freeze-dried form.

The solution is stable in the absence of air and is stored preferably between +1° C. and +25° C.

This adhesive composition is advantageously employed, after neutralization with an appropriate buffer before use, for bonding biological tissues to one another or to an implanted biomaterial.

Under these conditions, the neutralized polyaldehyde solution is stable for at least one day at ambient temperature.

The temperature of application of the polyaldehyde solution is between 20 and 45° C.

In the case of an implanted biomaterial the latter has functional groups which are reactive towards the polyaldehyde(s) present in the composition, which are formed in particular by amine-containing functional groups.

The material may include collagen or gelatin as described below.

A period of contact between the biomaterial and the adhesive composition of the order of 10 seconds to 3 minutes is advantageously envisaged before the in-situ application of the said material.

The bonding is produced gradually in general between 10 seconds and 3 minutes at physiological pH, at a temperature of the order of 37–40° C.

This bonding time and the time of in-vivo degradation of the adhesive formed can be controlled as a function of the concentration of the macromolecular polyaldehyde solution and according to the degree of oxidation of the polysaccharide as indicated below.

According to a second embodiment of the invention the adhesive composition includes a solution containing at least one biodegradable macromolecular polyaldehyde of natural origin as defined above and a solution of a collagen-based component.

According to the invention the term "collagen-based component" denotes collagen having at least partially lost its helical structure, by a heating operation or any other method, or alternatively native collagen.

In the case of heating in order to denature the helical structure of the collagen, the heating must be moderate and carried out under mild conditions, so as to avoid degradation by hydrolytic cleavage of the gelatin thus formed.

The collagen is unhydrolysed and mainly composed of α chains.

Within the meaning of the invention, α chains is understood to mean whole α chains or fragments which differ from whole a chains by the loss of a small number of amino acids.

The molecular weight of the whole a chains is generally approximately 100 kDa, that is to say from 95 to 130 kDa, depending on the case.

The term "unhydrolysed", as used according to the invention, means that less than 10% of the collagen-based chains have a molecular weight of less than approximately 100 kDa.

"Native collagen" is understood to mean collagen which has retained its original helical structure but which may have been modified chemically or alternatively treated in order to remove the telopeptides, as indicated hereinbelow.

The collagen employed according to the invention may be of human or animal origin, of type I, III or IV or originating from their mixture.

The original collagen may also be modified chemically by methylation, by succinylation or any other known method.

The collagen is preferably free of telopeptides, removed in particular by treatment with pepsin, so as to render it filterable on filters with a porosity suitable for sterilization (removal of microbes).

Commercial gelatins cannot be used for the purposes of the invention. Adhesives comprising such gelatins give gels which only become fluid and usable, in particular in syringes, at high temperatures greater than 45–50° C., which temperatures can cause burning and necrosis reactions of tissues (brain, nerve, intestine, cornea), whereas the objective is, on the contrary, to protect them.

In accordance with the invention the collagen is used in the form of aqueous solution.

For this purpose the collagen is solubilized in water in sterile conditions, by heating advantageously to an appropriate temperature of between 40 and 70° C.

The solubilizing conditions will be adapted as a function of the collagen employed.

The gelatin preparation thus obtained can be subsequently subjected to a filtration in sterile conditions, while the temperature is maintained between 40 and 70° C.

The collagen-based solution is advantageously at physiological pH, in the presence or otherwise of a buffer, especially a phosphate buffer.

According to the invention the gelatin solution may be a solution of 10 to 20%, preferably 15% to 18%.

According to an alternative form of the invention, especially for gelatin preparations of high concentration in the region of 20%, which are difficult to filter, the solution may be prepared in sterile conditions and employed for obtaining directly an adhesive composition according to the invention.

According to this alternative form, for these high concentrations, the preparation may be obtained by freeze-drying a sterile dilute solution and then redissolving the sterile powder using sterile water in a sterile vessel, and this makes it possible to carry out the operation without risk of contamination.

In general, the collagen is heated above 37° C. and thus loses most of its triple-helix helical structure. The final preparation can be likened to gelatin, but in which the molecular weight of the elementary chains is higher than or equal to 100 000 daltons, with less than 10% of the chains of lower molecular weight. This gelatin is thus unhydrolysed and is distinguished from the gelatins currently available commercially.

According to the invention, when the term "gelatin" is employed, it refers to such a preparation.

If it is desired to retain the helical structure of the collagen, especially in order to increase the in-vivo degradation time, the solution is not heated. It is then preferred to prepare less concentrated solutions, less than 5%, preferably between 0.2 and 5% approximately, in particular between 1 and 3%, starting from optionally pepsin-treated native collagen.

The process of crosslinking according to the invention includes the fact of mixing the abovementioned two solutions. A homogeneous mixture is advantageously produced.

The polyaldehyde is mixed with the collagen or gelatin in proportions of 0.5 to 10% by weight, preferably of 3 to 10% by weight.

The mixing of the abovementioned solutions is preferably performed at physiological, neutral pH and at a temperature of between 20 and 45° C., preferably of the order approximately of 37 to 42° C.

In the case of native collagen used according to a concentration of less than 5%, it is preferable to employ the collagen-based solution at ambient temperature, for example in the region of 20° C. to 30° C.

The adhesive composition and the process of crosslinking according to the invention can be used especially for stopping the bleeding of tissue wounds, for bonding biological tissues to one another or to an implanted biomaterial, for the cicatrization of surgical or chronic wounds, for the protection or leakproofing of sutures, for inhibition of the formation of postoperation adhesion or for the release of medications according to an extended release system, as well as in refractive surgery of the eye, in particular epikeratoplasty.

Depending on the applications, the implanted biomaterial consists of the adhesive itself, which is then used alone.

The invention finds a particularly advantageous application in the prevention of the formation of postoperation adhesions.

It also permits the adhesive bonding of lenses, in particular of lenses made of collagen, to the cornea in the field of the refractive surgery of the eye.

The invention thus provides a process for bonding a biomaterial to biological tissues comprising the fact of applying, at a temperature of between 200 and 45° C., a biodegradable macromolecular polyaldehyde of natural origin as defined above, in the form of an aqueous solution with the acidic pH naturally obtained or neutralized before use, to the said tissues and/or the said biomaterial, the biomaterial exhibiting functional groups, in particular amine-containing functional groups, which are reactive towards the said polyaldehyde.

According to another aspect, the invention provides a process for bonding biological tissues to one another or to an implanted biomaterial comprising the fact of mixing, at physiological, neutral pH, an aqueous solution of biodegradable macromolecular polyaldehyde of natural origin, as described above, with an aqueous solution of collagen-based component, as defined above.

The gel thus obtained is subsequently rapidly applied, that is to say preferably in less than one minute, to the said tissues and/or the said biomaterial, the biomaterial exhibiting functional groups, in particular amine-containing functional groups, which are reactive towards the macromolecular polyaldehyde, at a temperature of between 20° C. and 45° C., preferably 37° to 42° C., and then the combination is allowed to polymerize.

When the collagen-based component is native collagen, it is not necessary to heat the adhesive composition, which can then be applied at ambient temperature.

The solutions of the collagen-based component and of polyaldehyde can result from the redissolution in aqueous medium, buffered or otherwise, of the said components stored respectively in freeze-dried form.

On mixing the solution of collagen-based component and the solution of macromolecular polyaldehyde the homogeneous and viscous gel obtained sets solid gradually and hardens rapidly, adhering strongly, for example, to biological tissues to which it is applied.

According to the invention the crosslinking time can be controlled and increased beyond 30 seconds by decreasing the concentration of the polyaldehyde solution, in particular below 3%, for the same proportion of collagen.

For example, macromolecular polyaldehyde concentrations of between 3 and 0.5% make it possible to modulate the polymerization time of a 15% gelatin solution from 15 seconds to 5 minutes respectively.

The polymerization takes place gradually in general at physiological pH at a temperature of the order of 37 to 40° C.

According to an alternative form of the invention the in-vivo resorption time of the adhesive formed can also be adjusted by modifying the degree of oxidation of the polysaccharide used for obtaining the macromolecular polyaldehyde employed. The latter can thus be adjusted between 1 to 2 days and 30 to 60 days.

To this end it is advantageously possible to vary the final sodium periodate concentrations between 0.05M and 0.1M.

In general, the more the polyaldehyde concentration is increased, the more the resorption time also increases.

The invention also provides kits intended for surgical or therapeutic use, especially for the abovementioned applications.

According to a first embodiment the kit includes a solution containing at least one bioresorbable macromolecular polyaldehyde placed in a syringe.

An acidic aqueous solution containing 0.5 to 5% by weight of polyaldehyde(s) is preferably employed.

According to another embodiment of the invention the kit may be advantageously in the form of two syringes, each of which includes the collagen-based component solution and the macromolecular polyaldehyde solution, respectively. The collagen solution is, in its own syringe, at a physiological pH, with or without buffer (in particular a phosphate buffer).

The syringes are attached to a holding device equipped with means of mixing designed to be capable of mixing their contents extemporaneously in a homogeneous manner after they have been heated to the appropriate temperature of between 37 and 45° C., depending on the desired fluidity.

The kit may include a solution of 10 to 20% of unhydrolysed collagen, mainly composed of α chains, and a solution of 0.5 to 5% of polyaldehyde.

According to a preferred embodiment, a kit is provided comprising, on the one hand, collagen as an 18% solution and, on the other hand, 3% oxidized starch, in a ratio of 1/24.

If native collagen is employed, the kit comprises a 5% or less aqueous solution, preferably according to a concentration of 0.2 to 5%, more preferably 1 to 3%.

The adhesive composition according to the invention, and especially the kit described above, has the advantage of being capable of being stored between +1 and +25° C., preferably between +2 and +8° C.

Furthermore, according to the invention the crosslinking time can be shortened below 3 minutes and controlled according to the necessary requirements.

In parallel, the bonding strength developed by the product according to the invention is higher than that obtained with known adhesives, and especially fibrin adhesives, whilst retaining an excellent biocompatibility.

In addition, the invention advantageously offers the safety in use linked with the methods of preparation of the collagen which are effective in the removal of viruses and prions (Unconventional Transmissible Agents), especially through the use of an alkaline treatment. This rules out one of the major problems raised by fibrin adhesives.

Moreover, when compared with these fibrin adhesives, the viscosity of the adhesive composition according to the invention is higher, while remaining below 1000 centipoises, and thus facilitates its immediate adhesion.

The invention will be described in greater detail with the aid of the examples given below by way of guidance and without any limitation being implied.

EXAMPLE 1

Preparation of a solution of macromolecular polyaldehyde.

A solution of periodic acid or of sodium periodate is added, until a concentration of between 0.01 and 1M, preferably 0.25M, is obtained, to a solution of purified soluble starch or of dextran optionally exhibiting positive charges (amine groups) or negative charges (carboxylic or sulphonic groups) or any other functional group, the molecular weight of which may vary from 10 000 to 2 million daltons, at a concentration of 5% in water.

After 2 hours' contact at the laboratory temperature the solution is dialysed (or diafiltered with the aid of an ultrafilter) with a membrane with a cutoff threshold of 5000 daltons, against distilled water. The dialysis is continued until the dialysable products of the oxidation reaction and the reactants are completely eliminated, together with the iodine-containing derivatives formed during the reaction, or in excess.

It has been found that the polyaldehyde solution obtained becomes spontaneously acidic, which is favourable to its stability, and it is thus preferable not to add neutral buffer.

The final concentrated solution of the polyaldehyde polymer derived from the initial polysaccharide is next saturated with nitrogen by bubbling and packaged in sterile manner by filtration on a membrane of 0.2 g porosity.

The product is stable for at least a year between +4° C. and 25° C. in the absence of air.

In order to produce a kit according to the invention the solution prepared is packaged in syringes.

EXAMPLE 2
Preparation of a collagen solution.

An acidic solution of collagen at a concentration of 15% is prepared by dissolving an acidic collagen powder in water at a temperature of between 40° C. and 70° C. for 30 minutes.

The solution is neutralized to pH 7.5 by addition of normal sodium hydroxide solution as soon as the fluidity allows it.

In the case of bovine collagen of type I it may be acid-soluble (extracted from skins and tendons at acidic pH), or solubilized by digestion with pepsin, which makes it easier to filter later.

In the case of human collagens of placental origin, these may be prepared by extraction with pepsin according to the process described in application EP-A-0 204 035.

Other sources of collagen may, of course, be employed, among those known to the person skilled in the art.

The collagen solution thus heated, fluidified and neutralized, is then filtered in sterile manner on a membrane of $0.2\mu$ porosity, following prefiltrations on filters of progressively decreasing porosity, at an appropriate temperature between 40° C. and 70° C.

If filtration at a collagen concentration of 20% (or more) cannot be performed, the collagen solution is diluted before it is filtered.

According to an alternative form the sterile diluted solution is freeze-dried and the sterile powder is then redissolved using sterile water in a sterile vessel to the desired concentration.

The product is stable for at least a year at ambient temperature.

For the production of a kit according to the invention the collagen solution thus obtained can be easily distributed into syringes at a temperature of 40° C.

EXAMPLE 3
Preparation of an adhesive mixture.

A 0.5 ml syringe of 5% macromolecular polyaldehyde according to Example 1 and a 2 ml syringe of 15% collagen, according to Example 2, are prepared. Each of the syringes is attached to a holding device equipped with a mixer designed to be capable of mixing their respective content homogeneously after having heated them to a temperature of 40° C. to 42° C., or even 45° C. if a higher fluidity is desired.

The homogeneous and viscous gel obtained at the outlet sets solid at the same temperature, gradually from 15 to 30 seconds at physiological pH and hardens rapidly, adhering strongly to the biological tissues to which it is applied.

If the mixture is applied to a tissue surface or to a wound whose temperature is lower than 37° C. the polymerization induced by the chemical reaction between the aldehyde functional groups and the amine functional groups of the collagen is supplemented by a solidification resulting from the gelling of the collagen below 37° C.

The polymerization time can be increased beyond 15 seconds by diluting the macromolecular polyaldehyde below 5% or by employing a quantity smaller than 0.5 ml per syringe for 2 ml of collagen.

Macromolecular polyaldehyde concentrations of between 5 and 0.5% allow the polymerization time to be modified from 15 seconds to 5 minutes respectively.

It is also possible to employ a 5% solution of less oxidized polysaccharide, prepared, for example, with a final sodium periodate concentration of between 0.05M and 0.1M, as an alternative form of Example 1.

ADHESIVENESS TEST

The strength developed by the tissue adhesive thus prepared is measured by applying the mixture described above between two 6.25 $cm^2$ strips of pig skin, themselves joined separately by adhesive bonding with an acrylic adhesive on the epidermis side to two platens of a tensimeter.

After the mixed and fluid product is applied at 40° C. to each of the two strips on the dermis side, the two platens are immediately brought together to compress the whole with a force of 4 newtons for 1 minute and incubation is then carried out at 37° C. for 30 minutes.

When the platens are gradually separated, the tensile strength of the two strips is measured.

The force measured is 7.26 newtons. The work supplied to counteract the resistance to stretching is 10.96 millijoules.

In the same conditions "Tissucol" fibrin adhesive gives a force of 6.30 newtons and of 11.25 millijoules.

EXAMPLE 4

The force or work of Example 3 can be increased twofold or threefold by increasing the concentration of the collagen or of the macromolecular polyaldehyde as illustrated below:

A 0.5 ml syringe of a 5% solution of macromolecular polyaldehyde according to Example 1 and a 2 ml syringe of 20% collagen, according to an alternative form of Example 2, are prepared.

The procedure is as in Example 3.

In the adhesiveness test the force measured is 12.15 newtons and the work supplied to counteract the resistance to stretching is 27.72 millijoules.

EXAMPLE 5
Adhesive bonding of a lens made of collagen with a solution of macromolecular polyaldehyde to a rabbit cornea and to a nonhuman primate cornea.

To perform the adhesive bonding of a lens made of collagen, the lids are kept open with a blepharostat, the epithelium is removed from the cornea over a region that is wider than the diameter of the lens and the region from which the epithelium has been removed is then carefully washed to remove cell debris.

The 2.5% or 5% solution of polyaldehyde prepared according to the procedure of Example 1 is deposited in the concave face of the lens until the concavity of the latter is completely filled with the polyaldehyde solution.

After 30 seconds to 2 minutes of contact, the cornea surface is dried, the excess polyaldehyde solution is removed by aspiration and the concave face of the lens is then placed over the cornea, care being taken to centre the lens in relation to the optical axis.

The edge of the lens is correctly flattened down against the cornea with the aid of a spatula.

After 5 minutes' contact it is possible to mobilize the eyeball by means of a spatula placed on the lens.

In these conditions the use of macromolecular polyaldehyde at a concentration of between 2.5 and 5% does not result in any clinical inflammatory reaction on the anterior structures of the eye: cornea, conjunctiva, iris, eyelids, either in the albino rabbit (New Zealand) or in the nonhuman primate (Macaccus cynomolgus).

This absence of toxic reactions or of local irritation emphasizes the advantage of the adhesive composition according to the invention when compared with the use of the traditional crosslinking agents of the prior art for the preparation of tissue adhesives.

EXAMPLE 6

Prevention of the formation of post-operation adhesions.

The experimental model employed for demonstrating the properties of the adhesive according to the invention in the prevention of postoperation adhesions has been published by Elisabeth Harris and by George Rodeheaver's team (Surgery, 117, 6, 663–669, 1995).

The protocol described in this publication has been used on groups of 10 rats.

The tests consist in creating an abrasion and a dehydration on 2-cm$^2$ areas of peritoneal wall and of caecum, in contact with one another.

The group of control rats does not receive any product for protection of the lesions thus created; it is compared with the group of rats which receives from 1 ml to 2 ml of the tissue adhesive of the invention according to Example 3, by employing a kit including two syringes as described in this example, the adhesive being applied to each of the two lesions facing one another.

After 7 days' wait, in accordance with the published protocol, the results are clear:

No adhesion is observed between the two injured surfaces in the group of rats treated with the tissue adhesive according to the invention.

The group of control rats, not treated with the tissue adhesive of the invention, shows adhesions in the case of each of the 10 rats, the characteristics of which are identical with the results published in Surgery 117, 6, 663–669, 1995, referred to above.

From this same publication it follows (Table II, page 667) that the fibrin adhesive (Fibrin sealant) is not effective for completely inhibiting the formation of postoperation adhesions.

The antiadhesion properties demonstrated in the case of the tissue adhesive of this invention are particularly surprising when they are compared with those of the fibrin adhesives which do not have these properties.

According to the invention the adhesive composition forming an antiadhesion barrier can be applied in a precise spot, including by injection through a catheter, without risk of seeing this barrier move, which reinforces the safety and the effectiveness for the patient being treated.

EXAMPLE 7

Influence of the concentration of macromolecular polyaldehyde on the reactivity time of the adhesive composition according to the invention An adhesive composition is prepared based, on the one hand, on 16.5% collagen and, on the other hand, on 3.3% oxidized starch in liquid form, pH 3.3 (mean concentration determined by measuring the refractive index (3.1%) and by controlling the dry matter (3.5%)).

In this study, the oxidized starch is diluted in water to 1%, 0.75% and 0.5% respectively.

Furthermore, the starting point is collagen solutions with different pH values, in the presence of phosphate buffer.

The results obtained are shown in Table 1 below:

TABLE 1

| Collagen pH | Phosphate concentration (M) | Concentration of oxidized starch (final concentration) | Polymerization time of the mixture |
|---|---|---|---|
| 7.44 | 0.05 | 1% (0.2%) | 45 sec. |
|  |  | 0.75% (0.15%) | 1 min. and 5 sec. |
|  |  | 0.5% (0.1%) | 3 min. |

TABLE 1-continued

| Collagen pH | Phosphate concentration (M) | Concentration of oxidized starch (final concentration) | Polymerization time of the mixture |
|---|---|---|---|
| 7.08 | 0.02 | 1% (0.2%) | 2 min. |
|  |  | 0.75% (0.15%) | 2 min. and 30 sec. |
|  |  | 0.5% (0.1%) | 5 min. |
| 7.33 | 0.02 | 1% (0.2%) | 1 min. and 15 sec. |
|  |  | 0.75% (0.15%) | 2 min. |
|  |  | 0.5% (0.1%) | 4 min. |

These results show that the adhesive mixture hardens more rapidly as the concentration of oxidized starch and the pH of the mixture increase.

The oxidized starch concentrations of 1% and 0.75% lead to similar results, to within about 30 seconds. In contrast, a substantial difference is recorded between the 0.75% and 0.5% concentrations.

The combined gels exhibit good cohesion and they have an elastic appearance which becomes more pronounced as the oxidized starch concentration decreases, this difference being lasting over time.

The gel with 0.5% oxidized starch exhibits high elasticity.

The standard 3% oxidized starch concentration leads, for its part, to a highly resistant gel with a lower elasticity. The gel increases its elasticity with oxidized starch concentrations of the order of 1% or less. This property can be advantageous in numerous applications.

EXAMPLE 8

Influence of the concentration of buffer and of the pH of the collagen on the reactivity time of the adhesive composition according to the invention An adhesive composition is prepared based, on the one hand, on approximately 17% collagen and, on the other hand, on 3.3% oxidized starch in liquid form, pH 3.3, as in Example 7.

A phosphate buffer is added to the collagen according to concentrations varying from 0.01M to 0.1M and a phosphate-free collagen control is provided, adjusted to the same pH values.

The influence of the pH of the collagen is studied in parallel, by preparing solutions with a pH varying from 6.9 to 7.45.

The results obtained are shown in Table 2 below.

TABLE 2

| Collagen concentration (%) | Collagen pH | Phosphate concentration M | Polymerization time of the mixture | pH after mixing with oxidized starch |
|---|---|---|---|---|
| 17 | 7.12 | 0 | 45 sec. | 6.75 |
| 17.3 | 7.44 | 0.05 | 18 sec. | 7.15 |
| 17 | 7.45 | 0.1 | 15 sec. | 7.30 |
| 16.6 | 7.05 | 0 | 1 min. and 20 sec. | 6.60 |
| 16.8 | 7.25 | 0 | 1 min. and 05 sec. | 6.69 |
| 16.9 | 7.06 | 0.05 | 33 sec. | 6.94 |
| 16.9 | 7.36 | 0.05 | 17 sec. | 7.11 |
| 16.6 | 6.95 | 0.01 | 1 min. | 6.72 |
| 16.7 | 7.08 | 0.02 | 40 sec. | 6.92 |
| 17 | 7.33 | 0.02 | 28 sec. | 7.02 |

It is found that the reactivity of the mixture increases with the pH of the collagen and its buffering power.

EXAMPLE 9
Preparation of an adhesive mixture from native collagen

Use is made of collagen, dissolved by digestion with pepsin and purified, in aqueous solution containing 9 g/l of sodium chloride adjusted to pH 7, according to a concentration of 2%.

Collagen which is unmodified chemically or which is modified by succinylation or methylation can be used without distinction in this example. In all cases, it has retained its helical structure.

The product is distributed under sterile conditions in a 2 ml syringe stored at +4°C.

A 1% oxidized starch solution is prepared by dissolving acidic freeze-dried oxidized starch powder with a 0.2M phosphate buffer, pH 7.50. A 0.5 ml syringe is prepared.

The two collagen and starch syringes are combined in a kit similar to Example 3, heated to ambient temperature (in the region of 20° C.).

In order to evaluate the adhesive strength of the mixture obtained from this kit, the adhesiveness test according to Example 3 is carried out with 6.25 $cm^2$ strips of pig skin.

The results obtained are as follows:

The force measured is 4.5 newtons. The work supplied to resist stretching is 3.15 millijoules.

What is claimed is:

1. Biocompatible, bioresorbable and nontoxic adhesive composition for surgical and/or therapeutic use, especially for the bonding of biological tissues to one another or to an implanted biomaterial comprising at least one biodegradable macromolecular polyadehyde of natural origin in aqueous solution and a collagen-based component dissolved in aqueous medium selected from the group consisting of:
    unhydrolysed collagen having at least partially lost its helical structure, mainly composed of α chains, and
    native collagen according to a concentration of less than 5%.

2. Adhesive composition according to claim 1 wherein at least one biodegradable macromolecular polyaldehyde of natural origin is at the acidic pH naturally obtained.

3. Adhesive composition according to claim 1, wherein the polyaldehyde comprises an oxidized polysaccharide or mucopolysaccharide.

4. Adhesive composition according to claim 3 wherein the polysaccharide or mucopolysaccharide is selected from the group consisting of starch, dextran, agar, cellulose, chitin, chitosan, alginic acid, glycosaminoglycans, hyaluronic acid, chondroitin sulphate and their derivatives.

5. Adhesive composition according to claim 4 wherein the polysaccharide is selected from the group consisting of starch and dextran.

6. Adhesive composition according to claim 1, wherein the polyaldehyde comprises a polysaccharide or mucopolysaccharide oxidized with periodic acid or one of its salts.

7. Adhesive composition according to claim 4, wherein the polysaccharide has a molecular weight of between approximately 10 000 and 2 million daltons.

8. Adhesive composition according to claim 1, comprising it includes an aqueous solution of polyaldehyde(s) according to a concentration of 0.5 to 5% by weight.

9. Adhesive composition according to claim 1, wherein the aqueous solution is obtained by dissolving a polyaldehyde in acidic freeze-dried form in water or with a physiological buffer.

10. Adhesive composition according to claim 1, further comprising a solution of unhydrolysed collagen having at least partially lost its helical structure according to a concentration of 10 to 20%.

11. Adhesive composition according to claim 1, further comprising an aqueous native collagen solution according to a concentration of 0.2 to 5%.

12. Adhesive composition according to claim 1, wherein, for mixing, the proportion of the polyaldehyde in relation to the collagen is from 0.5 to 10% by weight.

13. Adhesive composition according to claim 1, wherein the composition is resorbable in the body between 1 to 2 days and 30 to 60 days.

14. Process for the preparation of a biocompatible, bioresorbable and nontoxic adhesive for surgical and/or therapeutic use intended to be applied to tissues and/or a biomaterial, comprising mixing a collagen-based component dissolved in aqueous medium selected from:
    unhydrolysed collagen having at least partially lost its helical structure, mainly composed of α chains,
    native collagen according to a concentration of less than 5% prior to its crosslinking, with at least one biodegradable macromolecular polyaldehyde of natural origin in aqueous solution.

15. Process according to claim 14, characterized in that the mixture is produced at a temperature of between 20 and 45° C.

16. Process according to claim 15, characterized in that the mixture is produced at a temperature of the order of 37 to 42° C.

17. Process according to claim 14, characterized in that the mixture is produced at a physiological, neutral pH.

18. Process according to claim 14, characterized in that the crosslinking is carried out in less than 5 minutes.

19. Kit including a biocompatible, bioresorbable and nontoxic adhesive composition, intended for a surgical and/or therapeutic use comprising:
    an aqueous solution of a collagen-based component selected from
    unhydrolysed collagen having at least partially lost its helical structure, mainly composed of α chains,
    native collagen according to a concentration of less than 5%,
    an aqueous solution containing at least one biodegradable macromolecular polyaldehyde of natural origin, and
    means of mixing for extemporaneously mixing the said solutions.

20. Kit according to claim 19, characterized in that it is in the form of two syringes equipped with means of mixing, in which one of the syringes contains the collagen-based component solution and the other contains the macromolecular polyaldehyde solution.

21. Kit according to claim 19, characterized in that it includes an aqueous solution containing at least one biodegradable macromolecular polyaldehyde of natural origin at the acidic pH naturally obtained.

22. Kit according to claim 19, characterized in that it includes a 0.5 to 5% polyaldehyde solution.

23. Kit according to claim 21, characterized in that the polyaldehyde solution is obtained by dissolving a polyaldehyde in acidic freeze-dried form in water or with a physiological buffer.

24. Kit according to claim 19, characterized in that it includes a 10 to 20%, preferably 15–18%, solution of unhydrolysed collagen having at least partially lost its helical structure, mainly composed of α chains.

25. Kit according to claim 19, characterized in that it includes, on the one hand, unhydrolysed collagen having at least partially lost its helical structure, mainly composed of α chains, as an 18% aqueous solution, and, on the other hand, oxidized starch as a 3% aqueous solution, according to a 1/24 ratio.

26. Kit according to claim 19, characterized in that it includes an aqueous native collagen solution according to a concentration of 0.2 to 5%, preferably 1 to 3%.

27. Kit according to claim 19, characterized in that the solution or solutions are maintained at a temperature of between +1 and 25° C., preferably between +2° C. and +8° C.

28. Process for bonding a biomaterial to biological tissues comprising applying an aqueous solution containing at least one biodegradable macromolecular polyaldehyde of natural origin at a temperature of between 20 and 45° C. to the tissues and/or to the biomaterial, the biomaterial exhibiting functional groups which are reactive towards the said polyaldehyde.

29. Process according to claim 28, for the bonding of a lens made of collagen.

30. Process for bonding biological tissues to one another or to an implanted biomaterial, comprising mixing at physiological, neutral pH, an aqueous solution of a collagen-based component selected from:

unhydrolysed collagen having at least partially lost its helical structure, mainly composed of a chains, native collagen according to a concentration of less than 5%, and an aqueous solution containing at least one biodegradable macromolecular polyaldehyde of natural origin;

applying rapidly the gel obtained to the said tissues and/or the said biomaterial, the biomaterial exhibiting functional groups, which are reactive towards the said macromolecular polyaldehydes, at a temperature of between 20 and 45° C.; and allowing the said mixture to polymerize.

31. Process according to claim 28, characterized in that use is made of an aqueous polyaldehyde solution with the acidic pH naturally obtained.

32. Process according to claim 28, characterized in that use is made of an aqueous polyaldehyde solution with the pH neutralized beforehand.

33. Process according to claim 28, characterized in that, in the case of unhydrolysed collagen having at least partially lost its helical structure, mainly composed of α chains, application is carried out at a temperature of between, 37 and 42° C.

34. Process according to claim 20, characterized in that, in the case of native collagen, application is carried out at ambient temperature.

35. Process according to claim 14, characterized in that use is made of an aqueous solution of macromolecular polyaldehyde at the acidic pH naturally obtained.

36. Process according to claim 14, characterized in that the biodegradable macromolecular polyaldehyde is oxidized starch.

37. Process according to claim 14, characterized in that the concentration of the aqueous solution of polyaldehyde(s) is of 0.5 to 5% by weight.

38. Process according to claim 14, characterized in that the aqueous solution is obtained by dissolving a polyaldehyde in acidic free-dried form in water or with a physiological buffer.

39. Process according to claim 14, characterized in that the concentration of the solution of unhydrolysed collagen having at least partially lost its helical structure is of 10 to 20%.

40. Process according to claim 14, characterized in that the concentration of the aqueous native collagen solution is of 0.2 to 5%.

41. Process according to claim 14, characterized in that the proportion of the polyaldehyde in relation to the collagen is from 0.5 to 10% by weight.

42. Process according to claim 30, characterized in that use is made of a 0.5 to 5% polyaldehyde solution.

43. Process according to claim 30, characterized in that use is made of a 10 to 20%, preferably 15–18%, solution of unhydrolysed collagen having at least partially lost its helical structure, mainly composed of α chains.

44. Process according to claim 30, characterized in that use is made of, unhydrolysed collagen having at least partially lost its helical structure, mainly composed of α chains, as an 18% aqueous solution, and, oxidized starch as a 3% aqueous solution according to 1/24 ratio.

45. Process according to claim 30, characterized in that use is made of aqueous native collagen solution according to concentration of 0.2 to 5%, preferably 1 to 3%.

46. Process according to claim 30, characterized in that use is made of an aqueous polyaldehyde solution with the acidic pH naturally obtained.

47. Process according to claim 30, characterized in that use is made of an aqueous polyaldehyde solution with the pH neutralized beforehand.

48. Process according to claim 28 wherein the biomaterial exhibits amine-containing functional groups which are reactive to the polyaldehyde.

49. A process according to claim 14, wherein the polyaldehyde comprises an oxidized polysaccharide or mucopolysaccharide.

50. A process according to claim 14, wherein the polysaccharide or mucopolysaccharide is selected from the group consisting of starch, dextran, agar, cellulose, chitin, chitosan, alginic acid, glycosaminoglycans, hyaluronic acid, chondroitin sulphate and their derivatives.

51. A process according to claim 14, wherein the polysaccharide is selected from the group consisting of starch and dextran.

52. A process according to claim 14, wherein the polyaldehyde comprises a polysaccharide or mucopolysaccharide oxidized with periodic acid or one of its salts.

53. A process according to claim 14, wherein the polysaccharide has a molecular weight of between approximately 10000 and 2 million daltons.

54. A process according to claim 15, characterized in that it includes, on the one hand, unhydrolysed collagen having at least partially lost its helical structure, mainly composed of a chains, as α 18% aqueous solution, and, on the other hand, oxidized starch as a 3% aqueous solution, according to a 1/24 ratio.

55. Kit according to claim 19, wherein the polyaldehyde comprises an oxidized polysaccharide or mucopolysaccharide.

56. Kit according to claim 19, wherein the polysaccharide or mucopolysaccharide is selected from the group consisting of starch, dextran, agar, cellulose, chitin, chitosan, alginic acid, glycosaminoglycans, hyaluronic acid, chondroitin sulphate and their derivatives.

57. Kit according to claim 19, wherein the polysaccharide is selected from the group consisting of starch and dextran.

58. Kit according to claim 19, wherein the polyaldehyde comprises a polysaccharide or mucopolysaccharide oxidized with periodic acid or one of its salts.

59. Kit according to claim 19, wherein the polysaccharide has a molecular weight of between approximately 10000 and 2 million daltons.

60. Kit according to claim 19, comprising an aqueous solution of polyaldehyde(s) according to a concentration of 0.5 to 5% by weight.

61. Kit according to claim 19, wherein the aqueous solution is obtained by dissolving a polyaldehyde in acidic freeze-dried form in water or with a physiological buffer.

62. Process according to claim 39, wherein the polyaldehyde comprises an oxidized polysaccharide or mucopolysaccharide.

63. Process according to claim 60, wherein the polysaccharide or mucopolysaccharide is selected from the group consisting of starch, dextran, agar, cellulose, chitin, chitosan, alginic acid, glycoaminoglycans, hyaluronic acid, chondroitin sulphate and their derivatives.

64. Process according to claim 62, wherein the polysaccharide is selected from the group consisting of starch and dextran.

65. Process according to claim 30, wherein the polyaldehyde comprises a polysaccharide or mucopolysaccharide oxidized with periodic acid or one of its salts.

66. Process according to claim 65, wherein the polysaccaride has a molecular weight of between approximately 10000 and 2 million daltons.

\* \* \* \* \*